| United States Patent [19] | [11] Patent Number: 4,661,622 |
| Matsumoto | [45] Date of Patent: Apr. 28, 1987 |

[54] METHOD FOR PRODUCING COMPOSITE ESTER

[76] Inventor: Satoshi Matsumoto, No. 569-74, Kawajirimachi, Kumamotoshi, Kumamotoken, Japan

[21] Appl. No.: 824,663

[22] Filed: Jan. 31, 1986

Related U.S. Application Data

[63] Continuation-in-part of Ser. No. 694,594, Jan. 24, 1985, abandoned.

[30] Foreign Application Priority Data

Sep. 21, 1984 [JP] Japan ................................ 59-196772

[51] Int. Cl.$^4$ .............................................. C07C 67/08
[52] U.S. Cl. .................................... 560/199; 524/285; 524/296; 524/310; 560/91; 560/92; 560/99; 560/204
[58] Field of Search ..................... 560/91, 92, 99, 199, 560/204

[56] References Cited

U.S. PATENT DOCUMENTS

| 2,575,195 | 11/1951 | Smith | 560/199 |
| 2,628,974 | 2/1953 | Sanderson | 560/199 |
| 2,956,954 | 10/1960 | Hoare et al. | 560/199 |
| 3,194,764 | 7/1965 | Ouist et al. | 560/199 X |

Primary Examiner—Natalie Trousof
Assistant Examiner—Vera C. Clarke
Attorney, Agent, or Firm—Fred Philpitt

[57] ABSTRACT

A novel method for producing a composite ester from dibasic acid, diol and monovalent alcohol through a dehydrating esterification reaction in the first step and then alcohol removing ester interchange reaction in the second step.

8 Claims, No Drawings

METHOD FOR PRODUCING COMPOSITE ESTER

CROSS REFERENCE TO A RELATED APPLICATION

This application is a Continuation-in-part of copending application, Ser. No. 694,594, filed on Jan. 24, 1985, now abandoned.

BACKGROUND OF THE INVENTION

1. Field of the Invention

This invention relates to a novel method for producing known compounds useful as a plasticizer or lubricating oil. More particularly, this invention relates to a novel method for producing composite esters consisting of a dibasic acid, a diol, and a monofunctional alcohol component.

2. Description of the Prior Art

There have been known composite esters represented by a general formula:

$$R'O(COACOORO)_nCOACOOR' \quad (a)$$

wherein A is a straight chain or cyclic hydrocarbon residue of 0 to 6 carbon atoms with the proviso that A is a bond when the number of carbon atom is 0, R is a residual group of straight or branched chain diol or ester alcohol, and R' is a residual group of straight or branched chain alcohol of 4 to 10 carbon atoms and n is an integer of 1 to 6. For example U.S. Pat. No. 2,730,811 discloses a production of bis-compounds by stoichiometric reaction.

In Japanese Patent Application No. 151,688/1983, I have disclosed a method for producing predominantly a bis-compound by using a diester and a diol, and in Japanese Patent Application No. 135,272/1984, a polyvinyl chloride composition in which a composite ester containing an oligomer obtained by this method is used as a plasticizer.

It is known to obtain plasticizers or lubricating oils (hereinafter referred to as plasticizers, etc.) by conducting esterification reaction using a monobasic acid or a monovalent alcohol which is to become terminal groups in the production of a polyester from a dibasic acid and a diol, controlling the molecular weight of formed polyester to obtain various polyesters having different combinations of molecular weight as well as acid and alcohol components, and such plasticizers etc. are on the market. Plasticizer properties of these plasticizers products etc. however, are not always satisfactory.

According to the method of the above-mentioned United States Patent, it is extremely difficult to obtain bis compounds as a reaction product in a stoichiometric quantitative amount.

Namely, in the above-mentioned reaction, since there is no difference of reactivity between each acid and alcohol group of the compound, a mixture of oligomers wherein n is 1 to 6 is formed and a bis compound wherein n=1 is produced in an yield of only less than the half amount. Unlike the addition of a monofunctional alcohol in the above-mentioned production of a polyester from a dibasic acid and a diol, the present invention provides a method for producing the above-mentioned composite ester in which, starting from a dibasic acid represented by the formula HOOC—A—COOH wherein A is a straight chain or cyclic hydrocarbon of 0 to 6 carbon atoms, a diol represented by the formula HO—R—OH wherein R is a residual group of straight or branched chain diol or ether alcohol, and a monovalent alcohol represented by the formula R'OH wherein R' is a residual group of a straight or branched chain $C_4$–$C_{10}$ alcohol, there is obtained, as an intermediate, a diester of a dibasic acid with a diol and a monovalent alcohol represented by the formula R'OCOACOOROH (hereinafter referred to as ester alcohol), from which a composite ester is produced by carrying out alcohol removing ester-interchange reaction between that diester (ester alcohol) and a diester represented by the formula R'OCOACOOR' (hereinafter referred to simply as diester). This is represented by the following reaction formula;

HOCOACOOH + HOROH + R'OH ⟶ R'OCOACOOROH +

(I)        (II)        (III)        (IV)

R'OCOACOOR' + $H_2O$ (V)

R'OCOACOOROH +

(IV)

R'OCOACOOR' ⇌ R'OCOACOOROCOACOOR' + R'OH (V)        (VI)

In the equilibrated second step of the formulae, the product composite ester (VI) can be obtained by removing R'OH.

It is well known for dehydrating esterification reaction to use an excess alcohol to produce an ester from an acid and an alcohol. In a system wherein a dibasic acid (I), a diol (II), and a monovalent alcohol (III) are mixed, the reaction product is obtained in a stoichiometric amount of the three components when the equivalent of the alcohols (diol and mono-alcohol) is equal to the equivalent of the acid. When the dehydrating esterification reaction is carried out in the presence of a dehydrating esterification catalyst, reaction rate of esterification accompanying formation of water becomes extremely slow at the late stages of the reaction. Accordingly, it is necessary to carry out esterification reaction in the presence of an excess amount of alcohols.

However, if an excess alcohol is added, ester interchange between the products concurrently occurs and once formed products including bis-compound (VI) are changed to higher molecular weight products. At the same time, the ester alcohol (IV) is formed as a by-product in an amount corresponding to the excess amount of the added alcohol. Although this ester alcohol (IV) has a lower boiling point compared with the bis-compound (VI) and its removal could be possible by distillation under reduced pressure in some cases, it is very difficult to completely remove it by distillation. When it remains in higher boiling point ester products, OH equivalent of the product is increased. Also, when it is added to a polyvinyl chloride as a plasticizer, a stabilizer therein acts as an ester interchange catalyst to cause ester interchange reaction, particularly at high temperatures, to form low boiling or volatile R'OH. This can be a cause of foaming and volatile material formation in use at high temperatures. Accordingly, removal of the ester alcohol is absolutely necessary.

On the other hand, when an ester mixture of a lower acid value is made by reaction in stoichiometric amounts followed by alkali-washing or the like to avoid unfavorable ester alcohol formation, there are problems in preparation such as increased raw material requirement per product due to the loss of unreacted material which is removed, as well as difficulty of separation of oil and water on account of the presence of alkali salt which acts to assist in emulsification, and thus it is difficult to attain low acid value.

The present invention has been completed on the basis of a discovery that a composite ester (VI) is produced when the above-mentioned dibasic acid (I), diol (II) and monovalent alcohol (III) are esterified in a proper mol ratio in the presence of a dehydrating ester catalyst, and then alcohol removing ester-interchange reaction is carried out using a titanium catalyst such as titanium tetrabutoxide, titanic acid ester, or a catalyst such as divalent tin compounds. Namely, I have discovered, when removing low boiling materials without removing catalyst after the use of a titanium catalyst, that alcohol removing reaction proceed. Thus, I have discovered that the ester interchange reaction proceeds easily by removing the produced alcohol with stirring and heating at 120° to 200° C. under reduced pressure.

SUMMARY OF THE INVENTION

The present invention relates to a method of preparing a composite ester (VI) in which dehydrating esterification is carried out using an excess amount of alcohol to an acid equivalent from the beginning and then ester-interchange reaction is carried out between an ester alcohol (IV) produced in the first reaction and a diester of carboxylic acid (V).

The value of n and proportions of various materials having different n values vary depending on the mol ratios of the starting materials as well as the mol ratio of the ester alcohol (IV) and the diester (V). The relations of the mol ratios and the yields and proportions of various materials having different n values will be explained.

When a bis-compound is to be obtained, it is necessary to select an initial step production condition such that 1.5 to 3 equivalents, preferably 2 equivalents of the diester is formed per one mole of the ester alcohol in the first step, since the amount of oligomers having a value of n of 2 or greater varies with the mol ratio of the di-ester to the ester alcohol.

When the mol ratio in the reaction of a dibasic acid (I), a diol (II), and a monovalent alcohol (III) is 3–4:1:5–7, the reaction products in the first step are theoretically a mixture of 2 to 3 mols of diester (V) and one mole of the ester alcohol (IV). In this reaction, the acid is 6 to 8 (2×(3 to 4)) equivalents to alcohol of 7 to 9 (1×2+5 to 7) equivalents, i.e. the alcohol equivalent is in excess of the acid and hence low acid value ester reaction products may be readily prepared.

In the reaction of a dibasic acid (I), a diol (II) and a monovalent alcohol (III) of mol ratio of 2:1:3, the product of the first step is theoretically a mixed system of one mol of diester (V) and one mol of ester-alcohol (IV). In this reaction, 5 equivalents of the alcohol is used to 4 equivalents of the acid. Thus, in the dehydrating esterification reaction, an acid value which is lower by an amount corresponding to the excess alcohol is easily attained, and separation of oil and water can be easily done by alkali washing, and all the problems in engineering to obtain the product can be solved.

When a mol ratio of a dibasic acid, a diol and a monovalent alcohol is 3:2:4 is used, the reaction product of the first step is theoretically a mixture of one mol of diester (V) and 2 moles of ester alcohol (IV), and in the next step of alcohol removing ester-interchange reaction, an oligomer mixture in which a compound of $n=2$ is predominant is produced. Similarly, when the mol ratio of dibasic acid, a diol, and a monovalent alcohol is 4:3:5, a mixture of one mol of diester (V) and 3 mols of ester alcohol (IV) is produced, and then an oligomer mixture in which a compound with $n=3$ is predominant is obtained by alcohol removing ester-interchange reaction.

Even when it is desired to separate the ester alcohol by itself, though some of the ester alcohol compounds could be purified by distillation, it is difficult in condition to produce pure ester alcohols by dehydrating esterification reaction. Namely, when one mol of a dibasic acid, one mol of a diol and one mol of a monovalent alcohol are reacted, the product is a mixture of high molecular weight compounds in which a plurality of molecules are condensed and which have terminal alcohol groups. To produce an ester alcohol in a good purity, it is preferred to use a mol ratio of dibasic acid (I) to diol (II) of 2:1 to 4:1 in the reaction. In this case, bis-compound (VI), i.e. the composite ester is the main by-product.

Further, when a large excess of a monofunctional alcohol is used, a diol is formed in the ester-interchange reaction, and it is removed from the system as an unreacted product. This is a cause of low yield. When the reaction is carried out in a manner in which portionwise addition is effected, that is, when only a part of alcohol is added at first depending on the progress of dehydrating esterification to increase reactivity of the diol, and then monofunctional alcohol is added as the esterification reaction proceeds further, the diol can be reacted quantitatively. It is necessary to select the mol ratio during the dehydrating esterification reaction to meet the requirements whether a high purity ester-alcohol is to be produced or a composite ester is to be produced.

Also, the ester-alcohol can be produced by reacting an excess amount of dibasic acid with ethylene oxide or propylene oxide, and remaining acid groups are esterified with dehydrating esterification.

Thus obtained mixture of ester-alcohol (IV) and diester (V) can be converted to a composite ester (VI) in accordance with the second step of the reaction formula described above. However, it is an equilibrated reaction, and proceeds in proportion to the rate of alcohol removal. Thus, stirring under reduced pressure is needed. In some case, leaving of diol can occur at the same time. Therefore, use of a heating condition between the boiling points of the monofunctional alcohol and the diol is preferred. Also, it is thought that the catalyst is active above about 100° to 120° C. and heating above this range is preferred. Preferred reaction catalysts include titanium tetrabutoxide and titanic acid esters as well as divalent tin compounds. The former two can be sometimes sufficiently active at 120° C., and the tin compounds are effective to the prevention of coloring. The ester alcohol when remains is not preferred in view of the raw material requirement and product purity. Thus it is preferred to effect the ester-interchange reaction sufficiently by heating up to 180° C. to 200° C./15 mmHg. As the titanium catalyst, the dehydrating esterification catalyst may be used as it is, and further addition may be done during the reaction.

The ester-interchange reaction can be monitored also by the amount of monofunctional alcohol distilled with the progress of the reaction. When the reaction is carried out at a high temperature under reduced pressure from the beginning, a diol is distilled out. In this case, the distillate can be recycled for more thorough reaction. The removal of the catalyst can be done in the same manner as the usual dehydrating esterification reaction. The catalyst is inactivated by addition of water, an adsorbent is added and suction filtration is carried out; and if further purification is required, alkali washing and hot water washing under heating is carried out to form low acid value ester.

The mol ratio of the ester-alcohol and diester in the ester-interchange reaction is an important factor to determine the proportion of the produced bis-compound oligomers in the product. When the ester-alcohol as it is is subjected to the reaction of alcohol removal, it is changed into a high molecular weight and highly viscous polyester. On the other hand, when a mixture with diester is subjected to ester-interchange, it becomes a mixture of (ester) oligomers having different n values depending on the molar ratio according to the following reaction.

$nR'OCOACOOROH + R'OCOACOOR' \rightarrow R'O(COACOORO)_nCOACOOR' + nR'OH$

As described above, although an ester oligomer with n=4 is to be formed from 4 moles of an ester-alcohol and one mol of a diester, a mixture of esters having different values of n is actually formed. From the result of liquid chromatographic separation, it is a mixture of compounds of n=1 to n=8 in which a compound of n=4 is predominant. On the other hand, to form a bis compound of n=1, it is necessary to use a greater mol ratio of the diester since a mol ratio of the ester-alcohol and the diester of 1:1 will result in oligomers of up to n=4, particularly those of n=2. Namely, at least 1.5 to 3 times the amount is necessary. With twice the amount, about 85% bis-compound is obtained. When the ratio is increased to 3 times the amount, the yield does not exceed 95% and by-product formation of oligomers cannot be eliminated.

Although the use of a greater amount of the diester is so much the better to increase the yield of the bis-compounds, recovered amount of diester is increased. It is preferred for the control of the molecular weight to control the mol ratio of ester-alcohol and diester by the addition of recovered diester to the reaction system.

The characteristic feature of the above-mentioned method for producing these composite esters is that a relatively low boiling composite esters having monofunctional alcohol terminals can be readily produced. Also, it is a method which enables stoichiometric reaction of a diol with a composite ester. The amount of alcohol produced by the alcohol removing ester interchange is decreased by an amount corresponding to the amount of monofunctional alcohol which is distilled off without pertaining the dehydrating esterification reaction. Thus, monofunctional alcohol and diol can be reacted quantitatively. When production of composite ester is attempted in accordance with a method of producing a polyester by adding monofunctional alcohol to regulate the molecular weight, terminal alcohols do not react by an amount of proportion corresponding to that of the formation of oligomer only with dehydrating reaction, and it is difficult to react lower alcohols quantitatively. By this reaction, composite esters having a lower alcohol terminal, particularly butanol can be readily prepared, and composite esters having low viscosity can be obtained. Low viscous composite esters show good plasticizing properties when used as a plasticizer. Also, in the method of the present invention, low acid values can be attained at the same reaction rate with usual dehydrating esterification reaction, since alcohol is in excess in the dehydrating esterification reaction. This product becomes to be of a lower OH value in the next alcohol removing ester-interchange reaction step, and composite esters may be made to be of lower viscosity and of high purity because of easy alkali washing and hot water washing.

Dibasic acids thus used in the reaction include oxalic acid, succinic acid, glutaric acid, adipic acid, azelaic acid, phthalic acid, hydrogenated phthalic acid or the like, and adipic acid is preferred.

The used diols having two functional groups include divalent alcohol having 2 to 8 carbon atoms having straight or branched chain, preferably, such as ethylene glycol, 1,2- or 1,3-propanediol, 2,2-dimethyl- or 2-methyl-2-ethyl-1,3-propanediol, 1,3- or 1,4-butanediol, or 1,6-hexanediol, or ether-alcohol having straight or branched chain, preferably diethylene glycol, dipropylene glycol, triethylene glycol or tripropylene glycol.

As the monofunctional alcohol, alcohols having $C_4$ to $C_{10}$ chain, or straight chain alcohols such as butyl, isobutyl, amyl, hexyl, heptyl, octyl, 2-ethylhexyl, decyl or the like, or alcohols obtained by oxo-process is used. n-Butanol is most preferred. In place of the difunctional alcohol, ethylene oxide or propylene oxide can also be used. In this case, after the oxide is added to excess acid with acceleration by stannic octylate to obtain a reaction product, dehydrating esterification is carried out by adding butanol to obtain a mixture of an ester-alcohol and a diester. Then a composite ester can be prepared by carrying out butanol removing ester-interchange reaction. At the time of reaction of an epoxide and an acid, an ether-alcohol is formed, and according to the results of liquid chromatography, this product is a mixture of various oligomers as when a mixture of propylene glycol and dipropylene glycol is used.

Following examples are to illustrate the present invention. Mol ratios, and combinations of an acid, a diol, and an alcohol is not limited to those of the examples.

EXAMPLE 1

To a mixture of 2.1 mol (306 g) of adipic acid, 0.7 mol (63 g) of 1.3-butanediol, and 0.7 mol (52 g) of n-butanol, was added 0.8 g of titanium tetrabutoxide dissolved in 60 g of azeotropic solvent of toluene. Resulting mixture was heated with stirring, and water is removed by azeotropic distillation. When 25% of the calculated amount of water was removed, addition of remaining 2.8 mols (207 g) of butanol was started ending when 90% of water was distilled off. In this reaction, calculated mol ratio of the diester to the ester-alcohol is 2:1. Dehydrating esterification reaction was continued for 14 hours and completed at an acid value of 0.25. The reacted liquid was transferred to a vessel for distillation under reduced pressure, to which 0.5 g of titanium solution was added, toluene distilled off, and 4 g of unreacted butanol was distilled off. While maintaining the temperature at 180° C. and a pressure of 250 mmHg to 50 mmHg, the distillate liquid was returned to the distillation vessel, and subjected to butanol removing ester-interchange reaction and reaction was continued until one equivalent of butanol was distilled. Finally, after 4.5 hours heating at a pressure of 18 mmHg, 51.5 g of butanol was recovered and reaction finished. After the temperature was decreased to 100° C., 5 ml of water was added and stirring was continued for one hour to inactivate the catalyst, and 10 g of active clay was added. The catalyst was removed by filtration. After completely removing alkaline matter using hot water containing 0.1 g of NaOH as well as hot water at 90° C., 206 g of dibutyl adipate was recovered by distillation under a reduced pressure. The remaining liquid consisted mainly of 1,3-butanediol bis-butyl adipate. The viscosity of the mixture at 21° C. was 50 c.p.s. The plasticizing efficiency herein means an amount of plasticizer which, when blended, gives the same hardness with that of 50 parts by weight of dioctyl phthalate (DOP). To polyvinyl chloride (molecular weight 1300), was blended 50 to 80 parts by weight of the resulting product together with a stabilizer. PVC sheets were made by milling and pressing to measure the hardness of the prepared sheets. Since a measured value of a sheet containing 40.5 parts by weight of it showed the same hardness with a sheet containing 50 parts by weight of DOP, the plasticizing efficiency of the product was expressed as 40.5. When 100 g of the mixed ester was distilled at a reduced pressure of 0.3 mmHg, 76.6 g of 1,3-butanediol bis-butyl adipate (1,6-hexanedioic acid 2-methyl-1,3-butanediyl dibutyl ester) having a boiling point of 228° to 233° C. and a viscosity of 55.3 c.p.s. at 21° C. was obtained.

The viscosity of 22 g of the remaining oil was 146 c.p.s., and from liquid chromatographic separation, it was found to be a mixture of oligomers wherein the compound of n=2 is predominant.

When plasticizing efficiency was measured, the bis-compound and by-product oligomer showed 42 and 45.2, respectively.

One millimeter thick sheets were prepared and their weight loss measured after heating at 160° C. for 2 hours were as low as 1% and 0.8% for sheets containing 50 phr and 1.2% and 0.7% for a sheets containing 80 phr, showing low volatility.

Using distilled products, heating tests in a hot wind circulating apparatus were conducted at 87° C. for 7 weeks and 100° C. for 3 weeks. As a result, sheets containing 80 phr kept a hardness of 76 and weight loss by heating of 1%. Since control sheets of DOP showed increase of hardness up to 94 and weight loss by heating of 6%, it is apparent that the heat-resisting property of the product is superior. In this test, a cold-resisting plasticizer DOA increases its hardness up to more than 95 after 5 weeks. On the other hand, flex-temperature measurement results of a 50 phr sheet according to JIS standard of the products of the present invention was −30.2° C. This is superior to −23.6° C. for those with DOP in low temperature resistance characteristic.

EXAMPLE 2.

After carrying out dehydrating esterification at the same component ratio as in Example 1, was added one mol equivalent of dibutyl adipate, and ester interchange was carried out. Dehydrating esterification was carried out by adding 0.8 g of titanium tetrabutoxide to 2.1 mol (306 g) of adipic acid, 0.7 mol (63 g) of 1,3-butanediol and 3.5 mols (259 g) of n-butanol to give a product having an acid value of 0.4. Then, were added 0.7 mol (180 g) of dibutyl adipate and 0.5 g of butyl titanate and 0.3 g of stannic octylate, and while removing butanol, ester interchange reaction was carried out at 250 mmHg, 160° C. to 17 mmHg, 180° C. for 4 hours with stirring under reduced pressure. After the same after-treatment as in Example 1 to recover dibutyl adipate, a composite ester was obtained. The bis-compound in the produced composite ester was 92% by weight and the viscosity of remaining 8% by weight of oil was 101 c.p.s. and liquid chromatographic separation results showed that it is oligomers wherein the compound of n=2 is predominant.

COMPARATIVE EXAMPLE 1

To a (2:1:2 mol) mixture of 1 mol (146 g) of adipic acid, 0.5 mol (45 g) of 1,3-butane diol and 1 mol (72 g) of n-butanol, was added 0.5 g of para-toluene sulfonic acid, and dehydrating esterification was carried out in the presence of a dehydrating solvent of toluene. Dehydrating esterification was carried out for 14 hours until acid value became 3 and further 34 hours, and then water washing and alkali washing was carried out. Oil/water separation was difficult by alkali washing and it could only be done after adding 1.2 liter of toluene.

REFERENTIAL EXAMPLE 2

To a (2:1:2 mol) mixture of one mol (146 g) of adipic acid, 0.5 mol (45 g) of 1,3-butanediol and 1 mol (72 g) of n-butanol, were added 0.5 g of titanium tetrahydroxide and 60 ml of toluene, and dehydrating esterification was carried out. When acid value was decreased to 6 after 14 hours, 72 g (1 mol) of butanol was added and dehydrating esterification reaction was carried out until an acid value becomes 0.3. After a treatment for catalyst removal, distillation was carried out under reduced pressure to produce 65 g (about 25 mol%) of dibutyl adipate. Further 36 g (13 mol%) of ester-alcohol distillate fraction (160° C.–180° C./0.5 mmHg) was obtained. The yield of high boiling products was 128 g, 55% of the theoretical amount. Liquid chromatographic analysis results of these products showed that n=1 compound is less than the half and they are a mixture of total of 6 kinds of compounds including those with n=2 or greater. The bis-compound which distilled at 235° to 245° C./0.5 mmHg reduced pressure was 56 g which is only 24% of the calculated amount and the oligomer product was 72 g (produced in greater amount than bis-compound). By the addition of an excess amount of butanol, dehydrating esterification reaction is completed swiftly. However, ester interchange reaction occurred concurrently, and the terminals of the diol do not react and and an ester alcohol distillate fraction is formed. The diol is azeotropically distilled too. Although the composition of higher boiling products varies depending on reaction time, temperature, molar ratio, and the like, it was noted that the weight % of the bis compound never exceeded the half amount.

EXAMPLE 3

To a mixture of 2.1 mol (307 g) of adipic acid, 1.4 mol (126 g) of 1,3-butanediol and 2.8 mol (207 g) of butanol, was added 60 g of toluene containing 0.8 g of titanium tetrabutoxide, and dehydrating esterification was carried out under azeotropic condition. Theoretically the amounts of resulting reaction products are 1.4 for the ester-alcohol vs. 0.7 for the diester. Dehydrating esterification reaction was completed at an acid value of 0.3, and then was added 0.8 g of butyl titanate, and by heating at 120° to 180° C. under a reduced pressure of 200 mmHg to 15 mmHg, reaction was carried out until the total amount of butanol formed reached 2 equivalents, and 101 g (97.5%) of composite ester was recovered.

The viscosity of reaction liquid after removal of catalyst was increased to a certain extent. 300 ml of toluene was added and hot alkali washing was carried out and lower boiling material was removed by heating the liquid to 240° C./0.4 mmHg. The viscosity of resultant oily matter was 350 c.p.s. at 21° C. and the plasticizing efficiency was 52. Liquid chromatographic separation results revealed that the product was a mixture of six kinds of composite esters herein n=2 compound was predominant.

EXAMPLE 4

To a mixture (acid:diol:monofunctional alcohol=5:4:6) of 2 mol (292 g) of adipic acid, 0.8 mol (72 g) of 1,3-butanediol, 0.8 mol (72 g) of 1,4-butanediol, and 2.4 mol (177 g) of n-butanol, were added 0.8 g of titanium tetrabutoxide, and 100 g of toluene, and dehydrating esterification reaction was carried out, and 4 mol (71 ml) of water was removed by distillation. Theoretically, the products are 1.6 mol of the ester alcohol and 0.4 mol of the diester. After addition of 0.5 g of titanium tetrabutoxide and 0.3 g of stannic octoate, ester-interchange reaction was carried out until butanol equivalent of 1.6 mol was obtained by heating at 120° to 180° C. under a reduced pressure of 200 mmHg to 15 mmHg with stirring. Recovered butanol was 114 g (96.6%). The products were a mixture of composite ester in which n=4 compound having a molecular weight of 1058 was predominant. Liquid chromatographic separation results revealed that it is a mixture of of high boiling materials having 8 kinds of peaks and a viscosity of 700 c.p.s. at 21° C. The plasticizing efficiency was 58. Although plasticizing property was somewhat inferior to that of DOP, heat-resistance property was superior since it showed a heat loss of 0.5% by weight at 160° C.

EXAMPLE 5

To a mixture of 2 mol (292 g) of adipic acid, one mol (76 g) of 1,2-propanediol, and 1 mol (74 g) of n-butanol, was added 60 g of toluene solution containing 0.8 g of titanium tetrabutoxide, and dehydrating esterification reaction was carried out. When the amount of water from azeotropic distillation was 35.7% (27 g), was added 2 mol (148 g) of butanol over 15 minutes, and the dehydrating esterification reaction was continued for 12 hours to obtain an acid value of 0.21. The product was transferred to a reduced pressure reactor, and after heating to 180° C. and distillation of toluene and unreacted n-butanol, pressure was gradually reduced, and reaction was continued until 1 mol of butanol was formed. Since this is a reaction between one mol of an ester-alcohol and one mol of a diester, and the ratio of ester interchange reaction with a diester to that with an ester alcohol is 2:1, it is considered that a bis-compound is formed in a greater amount. The viscosity of a higher boiling compound product was 75 c.p.s. In the actual distillation, the ratio in the mixture of the bis-compound (1,2-propanediol bis-butyl adipate (1,6-hexanedioic acid 1-methyl-1,2-ethynyl dibutyl ester)) having a boiling point of 225° to 230° C./0.2 mmHg to the remaining portion of the oligomers having n of 2 or greater was 45:55. The plasticizing efficiency of this mixture was 46 and plasticizing property was superior to that of DOP. The heat loss of a sheet after heating at 160° C. for 2 hours was 0.8% and heat-resisting property of this mixture was superior. The viscosity of a bis-compound obtained by distillation was 39 c.p.s. and the plasticizing efficiency was 40.5. Heat loss of sheets containing 50 phr and 80 phr at 160° C. after 2 hours were 2.5% and 1% by weight, respectively. Heat loss of a sheet after heat treatment for 7 weeks at 78° C. and additional 3 weeks at 100° C. was less than −2%. The surface hardness of a 80 phr sheet was 76. Thus, its flexibility was superior. The flex temperature of a 50 phr sheet as measured according to JIS was −28.2° C. Thus, resistance at low temperature was also superior.

EXAMPLE 6

To a mixture of 1.6 mol (350.4 g) of adipic acid, 0.8 mol (50 g) of ethylene glycol and 0.8 mol (59.2 g) of n-butanol, were added 0.8 g of titanium tetrabutoxide and 580 g of toluene, and dehydrating esterification reaction was carried out. When 23 ml (40%) of the reaction water was removed, remaining 1.6 mol (118.4 g) of n-butanol was added and dehydrating esterification reaction was carried out and acid value of 0.22 was obtained. The reaction liquid was transferred to a distillation vessel and after 0.5 g of titanium tetrabutoxide was added, heating was carried out with stirring at 120° C. to 180° C. under 200 mmHg to 15 mmHg, and 57 g of n-butanol was recovered. After alkali washing to remove the catalyst and washing with water in a manner already mentioned, distillation was carried out to recover slightly over 0.8 mol of dibutyl adipate, and then a higher boiling ester. This liquid product was a waxy ester mixture which solidified on standing. The liquid chromatographic separation result revealed that it was a mixture of composite esters having n of up to 6. The plasticizing efficiency was 46. The viscosity at 21° C. of ethylene glycol bis-butyl adipate (1,6-hexanedioic acid ethynyl dibutylester) having a boiling point of 235° to 240° C./0.4 mm was 34.2 c.p.s. The plasticizing efficiency was 42.5 and heat loss at 160° C. was 1.8% by weight and 1% by weight, showing superior plasticizing property and heat resistant property. The flex temperature of a 50 phr sheet according to JIS was −31.6° C., showing superior resistance at low temperature. Although pure bis-compound is an oily material, oligomers having n of 2 or greater have crystalline property. A mixture containing oligomers is waxy at room temperature.

Using pure bis-compounds obtained in Examples 1, 5, and 6, polyvinyl chloride sheets were prepared. Their mechanical strength was measured and shown in the following table. Compared with DOP, they showed superior plasticizing property. When the hardness is the same, all of them showed superior strength.

|  | COMPOUND | PHR | TENSILE STRENGTH (Kg/m$^2$) | ELONGATION (%) | 100% MODULUS | HARDNESS |
| --- | --- | --- | --- | --- | --- | --- |
| Example 1 | 1,3-BBBA | 50 | 2.18 | 371 | 0.68 | 75 |
| Example 1 | 1,3-BBBA | 40 | 2.55 | 311 | 1.05 | 84 |
| Example 5 | 1,2-PBBA | 50 | 2.21 | 374 | 0.68 | 75 |
| Example 5 | 1,2-PBBA | 40 | 2.40 | 304 | 0.97 | 84 |
| Example 6 | EBBA | 50 | 2.28 | 386 | 0.67 | 75 |

| | COMPOUND | PHR | TENSILE STRENGTH (Kg/m²) | ELONGATION (%) | 100% MODULUS | HARDNESS |
|---|---|---|---|---|---|---|
| Example 6 | EBBA | 40 | 2.66 | 317 | 0.98 | 83 |
| CONTROL | DOP | 50 | 2.26 | 368 | 0.82 | 82 |
| CONTROL | DOP | 40 | 2.56 | 293 | 1.37 | 91 |

EXAMPLE 7

To a mixture of 2.1 mol (306.6 g) of adipic acid, 0.7 mol (63 g) of 1,3-butanediol and 2.1 mol (214.2 g) of n-hexanol, were added 0.8 g of titanium tetrabutoxide, 0.2 g of stannic octylate and 80 g of toluene, and dehydrating esterification was carried out. When 37.8 ml of water was distilled out, 143 g of n-hexanol was added. An ester mixture was prepared such that the theoretical amount is 1.4 mol of diester to 0.7 mol of the ester alcohol. After acid value became 0.28, was added 0.5 g of butyl titanate, and at a reaction temperature of 180° C. under atmospheric or subatmospheric pressure, ester-interchange reaction was carried out and 71.4 g (93%) of n-hexanol was recovered. After treatment for removing catalyst, alkali washing and water washing were carried out and distillation was carried out under reduced pressure to provide 263 g (119%) of dihexyl adipate, 19.8 g of intermediate fraction and 252 g of residual portion. The viscosity of a higher boiling portion was 99 c.p.s. at 21° C. The plasticizing efficiency to polyvinyl chloride was 48 and heat loss of 50 phr sheet after heating at 160° C. for 2 hours was 0.6% by weight. A 150 g of remaining liquid was subjected to fractional distillation (240°-265° C./0.5 mm) and 138 g (92%) of 1,3-butanediol bis-n-hexyl adipate was obtained. It was revealed that the major part of the product is the bis-compound. The viscosity of bis compound at 21° C. was 90 c.p.s. and plasticizing efficiency was 47.

EXAMPLE 8

The plasticizing efficiency of 1,3-butanediol bis-2-ethylhexyl adipate prepared as in Example 1 using adipic acid (3 equivalents), 1,3-butanediol (1 equivalent) and 2-ethylhexanol (5 equivalent) was 45.2.

EXAMPLE 9

The plasticizing efficiency of 1,4-butanediol-bis-2-ethylhexyl adipate which was prepared in the same manner as in Example 1 using adipic acid (3 equivalents), 1,4-butanediol (1 equivalent) and 2-ethylhexanol (5 mol equivalent) and which contained also oligomers was 50, and it showed approximately the same plasticizing efficiency with DOP, and showed less than 1% heat loss. But it is crystalline at high temperatures.

EXAMPLE 10

The plasticizing efficiency of 1,6-hexanediol-bis-2-ethylhexyl adipate which was prepared in the same manner as in Example 1 using adipic acid (3 equivalents), 1,6-hexanediol (1 equivalent) and 2-ethylhexanol (5 mol equivalents) and which contained also oligomers was 46, and it was excellent in heat resisting property showing heat loss at 160° C. of less than 1%.

EXAMPLE 11

The plasticizing efficiency of a composite ester prepared from 3 equivalents of adipic acid, one mol equivalent of diethylene glycol, and 5 equivalents of 2-ethylhexyl adipate and which contains oligomers was 45.8.

EXAMPLE 12

A composite ester containing oligomers prepared from adipic acid (3 equivalents), dipropylene glycol (1 mol equivalent) and 2-ethylhexyl adipate (5 equivalent) showed a plasticizing efficiency of 48.5.

EXAMPLE 13

Dipropylene glycol bis-butyl phthalate containing oligomers prepared from phthalic acid (3 equivalents), dipropylene glycol (1 equivalent) and n-butanol (5 mol equivalents) showed a plasticizing efficiency of 54.4 and this value is lower than that of DOP. However, it showed superior heat resisting property as seen in less than 1% volatility at 160° C. for 2 hours.

EXAMPLE 14

After dissolving 2 mol (292 g) of adipic acid, 2 mol (143 g) of n-butanol and 150 g of toluene by heating, was added 0.5 g of stannic 2-ethylhexanoate, and then was added gradually 1 mol (58 g) of propylene oxide, and reaction was carried out at 60° C. with stirring. After 4 hours, were added 1 mol (74 g) of remaining n-butanol and 0.5 g of titanium tetrabutoxide as a dehydrating catalyst, and azeotropic dehydrating was carried out. After acid value of the product became 0.5, heating at 180° C. was carried out under 250 to 15 mmHg with stirring, and butanol formed as removed and reaction was completed. The product showed a viscosity of 70 c.p.s. which is higher to same extent, and a good plasticizing efficiency of 43 as well as good heat loss of 1.5% or smaller.

The liquid chromatographic separation results showed that the product is a mixture of eight overlapped peaks and judged to be a mixture of those formed from propylene glycol and those formed from dipropylene glycol.

EXAMPLE 15

Preparation of composite esters from ester-alcohol

The ester-alcohol can be obtained in the method of the present invention by not carrying out the alcohol removing ester-interchange reaction, or as an unreacted fraction in the ester-interchange reaction which distills between the bis compound and the starting diester. On the other hand, it can be obtained as an intermediate of direct alcohol removing ester-interchange reaction between the diester and the diol. Adipic acid 3-methyl-3-hydroxypropyl butyl ester (3-methyl-3-hydroxypropyl butyl adipate), an ester alcohol prepared from adipic acid, 1,3-butanediol, and butanol may be purified after dehydrating esterification as in Example 1, and catalyst removing treatment and then distillation. The boiling point is 155° to 160° C./0.2 mmHg. Using a mixture of 82.8 g of this product and 405 g of dibutyl adipate (mol ratio is 1:5.2) to which 0.5 g of butyl titanate was added, reaction was carried out under a reduced pressure of 20 mmHg and heating at 160° C. for 12 hours with stirring while removing 21.5 g (97%) of resulting butanol, and after completion of the reaction, catalyst removing alkali washing and water washing as well as distillation was carried out to obtain 342 g of DBA and 5.2 g of unreacted ester-alcohol and 94.9 g (75.8%) of 1,3-butanediol bis-butyl adipate having a boiling point of 235° to 245° C./0.8 mmHg and 7.6 g (8.4%) of a residual material which was considered to be an oligomer of n=2.

I claim:

1. A method for producing a composite ester represented by the formula $$R'O(COACOORO)_n COACOOR' \qquad (X)$$

wherein A is straight chain or cyclic hydrocarbon of 0 to 6 carbon atoms with the proviso that A is a bond when the number of carbon atoms is 0, R is a straight or branched chain alcohol residue of a diol or an ether-alcohol, R' is a straight or branched chain alcohol residue having 4 to 10 carbon atoms and n is an integer of 1, 2, 3 or 4 comprising:
  (a) subjecting a dibasic acid having the formula of HOCOACOOH, wherein A is as defined above, and a diol having the formula of HOROH, wherein R is as defined above, together with monovalent alcohol having the formula R'OH, wherein R' is as defined above, to a dehydrating esterification reaction, the mol ratio of said dibasic acid to said diol being in the range of 4:1 to 1:1 and the amount of said monovalent alcohol being in excess to said dibasic acid, to thereby form a monovalent alcohol diol diester of dibasic acid represented by the formula R'OCOACOOROH, wherein A, R, and R' are as defined above, and a monovalent alcohol diester represented by the formula R'OCOACOOR', wherein A and R' are as defined above,
  (b) effecting alcohol removing ester-interchange reaction between said monovalent alcohol diol diester and said monovalent alcohol diester using a titanium catalyst selected from the group consisting of titanium tetrabutoxide and an alkyl titanate to form said composite ester.

2. A method according to claim 1 wherein n is 1.

3. A method according to claim 1 wherein n is 1 and said dibasic acid is adipic acid.

4. A method according to claim 1 wherein n is 1 and said diol is ethylene glycol, 1,2- or 1,3-propylene glycol, 1,3- or 1,4-butanediol, 1,6-hexanediol or dipropylene glycol.

5. A method according to claim 1 wherein n is 1 and said monovalent alcohol is n- or iso-butanol, amyl alcohol, hexanol, 2-ethylhexanol, n-octanol or $C_7$ to $C_9$ alcohol prepared by oxo-process.

6. A method according to claim 1 wherein n is 1 and said mol ratio of the reaction of monovalent alcohol diol diester of dibasic acid is controlled by the addition of monovalent alcohol diester for further alcohol removing ester-interchange reaction.

7. A method according to claim 1 wherein n is 1 and alcohol removing ester interchange reaction is carried out at a mol ratio of monovalent alcohol diol diester of dibasic acid to monovalent alcohol diester of dibasic acid of from 1:4 to 4:1.

8. A method for preparing a composite ester according to claim 1 wherein n is 1 and said alcohol removing ester-interchange reaction is carried out at 120° to 180° C. under atmospheric or subatmospheric pressure.

* * * * *